United States Patent [19]

Goldstein

[11] Patent Number: 4,749,690

[45] Date of Patent: Jun. 7, 1988

[54] TREATMENT OF ALLERGY WITH THYMOPENTIN

[75] Inventor: Gideon Goldstein, Short Hills, N.J.

[73] Assignee: Ortho Pharmaceutical Corporation, Raritan, N.J.

[21] Appl. No.: 822,704

[22] Filed: Jan. 27, 1986

[51] Int. Cl.⁴ ............................................. A61K 37/02
[52] U.S. Cl. ....................................... 514/17; 514/885
[58] Field of Search ................................... 514/17, 885

[56] References Cited

U.S. PATENT DOCUMENTS 4,190,646  2/1980  Goldstein et al. ................. 530/330
4,298,523  11/1981  Hearner ............................. 530/330

OTHER PUBLICATIONS

*Stedman's Medical Dictionary*, 23rd ed., The Williams & Wilkins Co., Baltimore, p. 44.
Lau et al., *Chemical Abstracts*, 93, 97, (1980), Abst. No. 198145n.
*A Textbook of Medicine*, 5th ed., Edited by Cecil, W. B. Saunders Co., Philadelphia, Pa., 19141, pp. 358-541.
Roitt, *Immunology*, Gower Medical Publishing, London, England, 1985, pp. 19.2-19.11.
*Basic & Clinical Immunology*, 5th ed., Lange Medical Publications, Los Altos, Calif., 1984, pp. 500-509.

*Primary Examiner*—J. R. Brown
*Assistant Examiner*—F. T. Moezie
*Attorney, Agent, or Firm*—Geoffrey G. Dellenbaugh; Jason Lopow; Richard J. Grochala

[57] ABSTRACT

A method for treating allergy by administration of the peptide thymopentin.

10 Claims, 3 Drawing Sheets

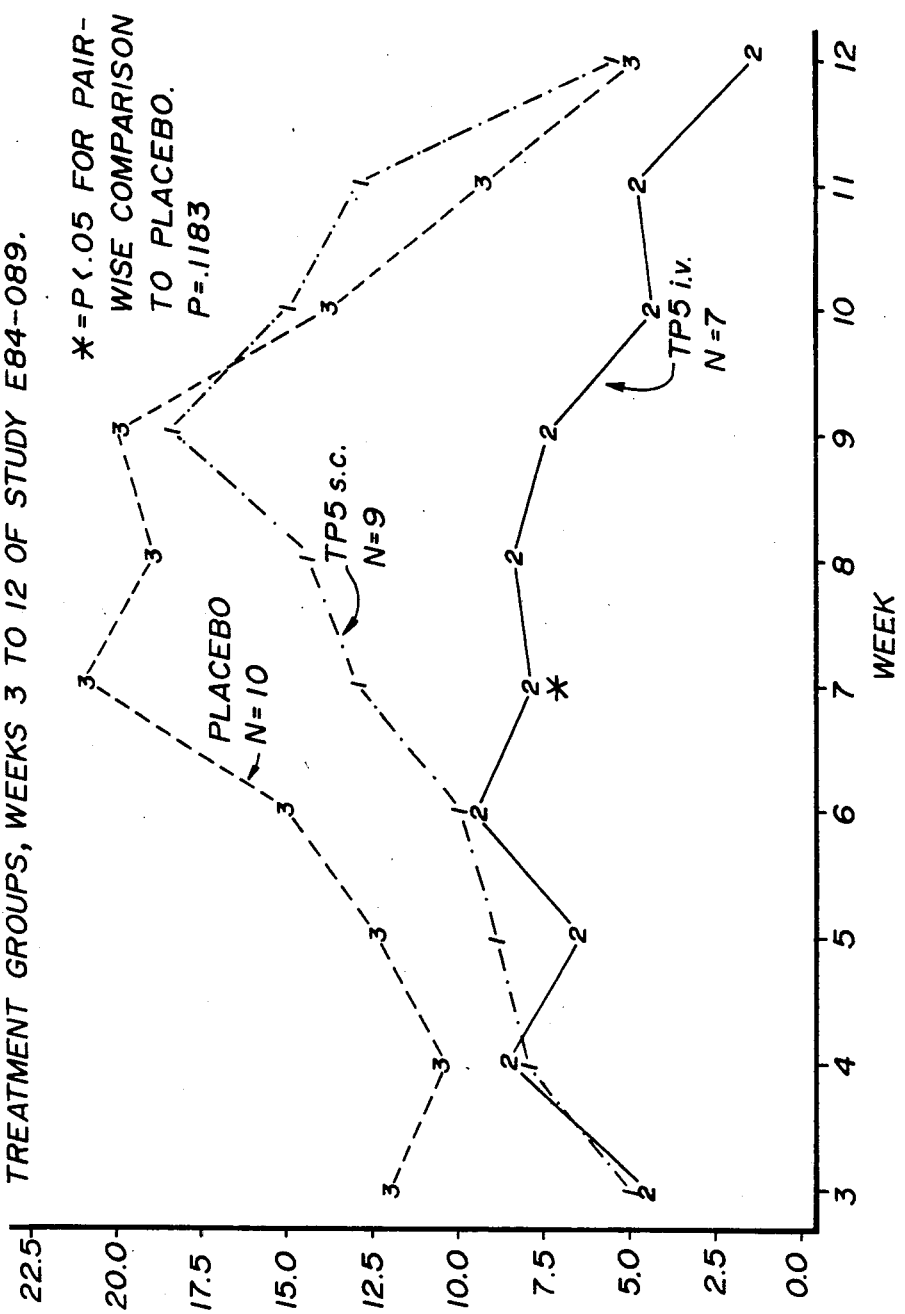

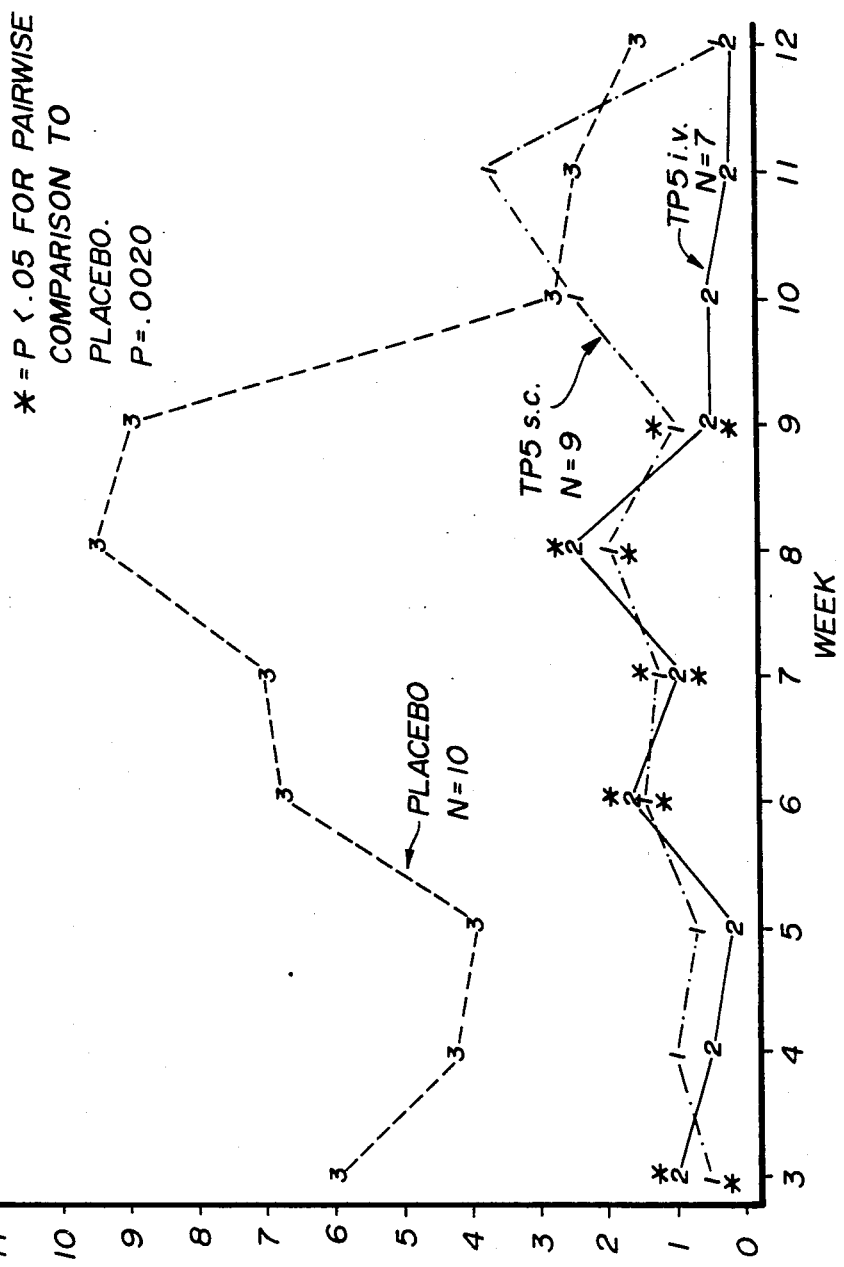

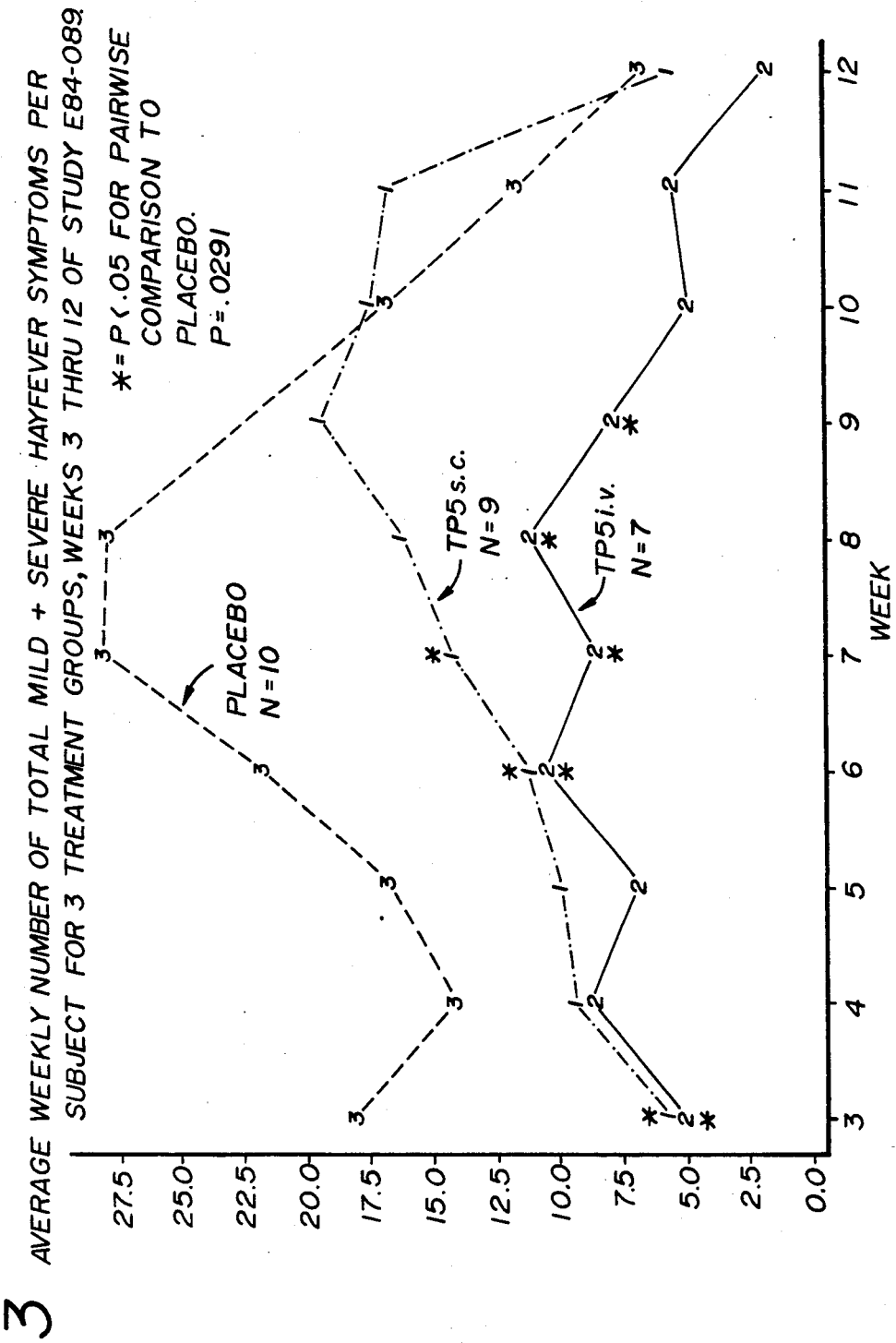
FIG-3 AVERAGE WEEKLY NUMBER OF TOTAL MILD + SEVERE HAYFEVER SYMPTOMS PER SUBJECT FOR 3 TREATMENT GROUPS, WEEKS 3 THRU 12 OF STUDY E84-089.

TREATMENT OF ALLERGY WITH THYMOPENTIN

BACKGROUND OF THE INVENTION

1. Field of the Invention

This invention relates generally to the treatment of allergy and in particular to the treatment of allergy with the peptide thymopentin.

2. Description of the Art

U.S. Pat. No. 4,190,646 describes the pentapeptide thymopentin, having the sequence H-ARG-LYS-ASP-VAL-TYR-OH. This pentapeptide has activity similar to the long chain polypeptide known as thymopoietin, disclosed in U.S. Pat. Nos. 4,002,740 and 4,077,949. Both thymopoietin and thymopentin selectively stimulate the differentiation of T lymphocytes. The U.S. Pat. No. 4,190,646 discloses that thymopentin is expected to have utility in the areas of thymic function and immunity. The various specific diseases or conditions which could be treated by thymopentin are described in this patent. Since the invention of thymopentin, considerable effort has been expended on studying its effect on a variety of immune-related disorders. A collection of some recent work in this area is contained in Survey of Immunologic Research, Volume 4, Supplement 1, 1985, entitled "Thymopentin in Experimental and Clinical Medicine". This volume is completely devoted to thymopentin and its relevance to treatment of immune disorders.

Sale of thymopentin (under the trademark "TIMUNOX") was commenced in Italy in the spring of 1985 for treatment of primary immune deficiency.

Although the Supplement referred to above evidences effectiveness of thymopentin in treatment of herpes and rheumatoid arthritis, there is no suggestion that it would be effective in treatment of allergy.

Nearly one in every ten persons in the United States suffers from symptomatic atopic disease, the most common being allergic rhinitis. Bronchial asthma and atopic dermatitis occur less frequently. Other types of allergic disorders include anaphylaxis, urticaria and periarteritis nodose. Immunologically, allergy is classified as a type I hypersensitivity reaction to environmental antigens (allergens) in genetically-susceptible individuals who produce IgE antibodies to these allergens. These IgE antibodies (fixed to mast cells) react with the allergen, triggering the release of histamine, leucotrienes, eosinophil chemotactic factor (ECF) and other mediators of allergic hypersensitivity. The action of these mediators on blood vessels, smooth muscles, and secretory glands is responsible for the clinical manifestation and pathologic features of the disease.

Conventional therapies for hay fever and other forms of allergic rhinitis typically include drugs such as antihistamines or corticosteroids, which act on the mediators, rather than the root cause of the disease. These drugs have various side effects which render them less than ideal, especially for long-term use. The other conventional therapy is immunotherapy, normally consisting of a program of desensitization injections to the appropriate allergens. Although such treatments attack the cause of the disease, they are time-consuming, costly, and painful. The responsible allergen(s) must be determined, typically by a series of skin tests, following which the patient must be subjected to the desensitization injections.

Significant benefit would be afforded those suffering from allergic rhinitis and other allergic disorders if a therapy could be made available which treated the root cause of the disease without the discomfort and inconvenience of desensitization injections.

SUMMARY OF THE INVENTION

It has now surprisingly been found that thymopentin is useful for treating allergy and in particular allergic rhinitis. In a double-blind study, thymopentin was found to be statistically significant compared to placebo in alleviating the symptoms of allergic rhinitis.

Accordingly, the present invention provides a method for palliating the symptoms of allergy in a subject having said symptoms which comprises administering to the said subject an effective allergy-palliating amount of thymopentin or a pharmaceutically-acceptable salt thereof. These symptoms include sneezing, runny nose, red eyes, itchy eyes, and cough for allergic rhinitis and other art-known symptoms for other allergic disorders. The symptoms of asthma, for example, include expiratory dyspnea, cough, overinflation of the lungs, and other symptoms generally attributable to partial bronchial airway obstruction. As used herein, the term "allergy" includes all immune reactions mediated by IgE. Allergic conditions amenable to treatment with thymopentin include allergic rhinitis, asthma, atopic dermatitis, and urticaria, for example.

BRIEF DESCRIPTION OF THE DRAWINGS

FIG. 1 shows the average weekly number of mild hay fever symptoms per subject for each treatment group (weeks three through twelve).

FIG. 2 shows the average weekly number of severe hay fever symptoms per subject for each treatment group (weeks three through twelve).

FIG. 3 shows the average weekly number of total (mild plus severe) hay fever symptoms per subject for each treatment group (weeks three through twelve).

DETAILED DESCRIPTION OF THE INVENTION

The practice of the present invention was demonstrated by a double-blind study involving three groups of patients suffering from hay fever. Each group was given a subcutaneous injection three times a week and an intravenous injection once a week; in the first group the first injection was thymopentin while the second was placebo, in the second group the first injection was placebo and the second thymopentin, while in the third group both injections were placebo. Based on patient assessment of five symptoms using the categories "none", "mild", and "severe", groups 1 and 2 experienced fewer symptoms than group 3. This difference was statistically significant for group 2. The application of the present invention is illustrated by the clinical study on thymopentin in the treatment of patients with Ragweed Hay Fever given in the Example which follows.

EXAMPLE

I. Patient Selection

Thirty (30) patients with a proven history of ragweed hay fever, who fulfill all of the inclusion criteria and none of the exclusion criteria, were enrolled in this single site study.

A. Inclusion Criteria

1. Males or females between the ages of 18 and 40 inclusive.
2. Female patients must be surgically sterile, or using acceptable non-steroidal forms of contraception; for women of child-bearing potential, a negative pregnancy test must be documented at the time of enrollment into the study.
3. History of moderate to severe ragweed hay fever for at least three years.
4. Skin test reactivity of at least 2+ to diluted whole ragweed extract by the prick test method.

B. Exclusion Criteria
1. Previous immunotherapy for allergic hypersensitivity.
2. Asthma (including ragweed pollen asthma).
3. Pregnancy
4. Significant cardiovascular, renal, hepatic, neurological, non-allergic gastrointestinal disease, or malignancy.
5. Patients who have received an investigational drug less than 30 days prior to admission.
6. Steroids, non-steroidal anti-inflammatory drugs, Cimetidine, Ranitidine, and other immunomodulatory agents within 60 days of the study.
7. Previous treatment with radiation or chemotherapy.

II. Description of Study

This invention was a placebo-controlled phase II safety and efficacy study of Thymopentin (TP5) in the treatment of patients with Ragwood Hay Fever.

A. Study Design

Thirty (30) patients were assigned to either TP5 or placebo according to a double blind randomization schedule. Ten (10) patients were assigned to each of three (3) treatment groups described as follows.

Group 1 received 1.0 ml TP5 (50 mg/ml) subcutaneously three (3) times per week and 5.0 ml placebo intravenously once weekly for twelve (12) weeks.

Group 2 received 1.0 ml placebo subcutaneously three (3) times per week and 5.0 ml TP5 (20 mg/ml) intravenously once weekly for twelve (12) weeks.

Group 3 received 1.0 ml placebo subcutaneously three (3) times per week and 5.0 ml placebo intravenously once weekly for twelve (12) weeks.

III. Procedures

1. Each patient received subcutaneous injections three (3) times per week and one intravenous injection per week for twelve weeks, according to the group randomization schedule described above.
2. All patients received a diary in which allergy medication (chlortrimeton) taken during the course of the study and symptoms related to Ragweed Hay Fever were documented. Patients received specific instructions pertaining to continued maintenance of their symptom and medication diaries. The diaries were reviewed weekly and returned upon termination of treatment.

V. Results

The results of this study were analyzed in several ways to evaluate the efficacy of thymopentin in the treatment of Ragweed Hay Fever symptoms.

Each of the thirty subjects recorded twice daily the occurrence of five symptoms using the mutually exclusive scores "none", "mild", and "severe". The efficacy of treatment was determined by comparison of the average weekly number of mild and severe symptoms per subject.

In one analysis, a score was created for each subject based upon the number of times certain symptoms were noted over the ten-week period of study. Each occurrence of a mild or severe symptom was scored as "1" and the average weekly score over the ten weeks for which data were collected was computed for each subject. Pair-wise comparisons were made among the three groups using a standard t-test. The results are summarized in Table I. Even this basic comparison, which is not weighted for severity of the symptoms, demonstrates some statistically significant differences. Group 2 (Thymopentin IV) had the lowest average weekly number of mild and severe symptoms and had a statistically significant difference from group 3 (the placebo group). Group 1 (Thymopentin subcutaneously) also had a smaller number of symptoms than the placebo group, although the difference from placebo is not statistically significant.

A more detailed analysis used a repeated measures analysis of variance, in which the total weekly symptoms were compared on a week-by-week basis. The results are presented in Table II and graphically in FIGS. 1 through 3. This analysis indicates high significance among the three groups with respect to severe symptoms and all symptoms. FIG. II in particular illustrates the effectiveness of Thymopentin administered either subcutaneously or intravenously in decreasing the number of severe hay fever symptoms.

Table III presents the mean weekly numbers of symptoms per subject for each of the three groups and each of the five categories of symptoms separately.

The present invention has been illustrated by the treatment of hay fever, a form of allergic rhinitis, but it is expected that one of skill in the allergy treatment art will readily recognize that the method can be straightforwardly applied to treatment of other allergic disorders. The preferred method of administration of thymopentin to achieve the desired result is parenteral, more preferably intravenous or subcutaneous, and most preferably intravenous. It is not believed, however, that the specific mode of administration is critical to the practice of the present method so long as an effective amount of thymopentin enters the blood stream. Applicants have found that 50 mg of thymopentin administered subcutaneously three times per week and 100 mg. of thymopentin administered intravenously once per week were effective regimens to palliate allergic symptoms. It is well within the skill of a practitioner in the anti-allergy art to determine appropriate doses of thymopentin and frequencies of administration to achieve the desired palliation. It is believed from about 50 mg to about 700 mg of thymopentin administered intravenously would be effective in the present method. For subcutaneous administration, those skilled in the art would recognize the necessity to increase the dose. Since thymopentin is a very safe drug, the only practical upper limit is dictated by optimum efficacy. All such doses, frequencies of administration, and modes of administration are intended to be included within the subject method.

The above example has been presented for illustrative purposes only and not to limit the scope of the present invention, which scope is set out in the following claims.

TABLE I

PAIRWISE GROUP COMPARISON OF AVERAGE WEEKLY NUMBER OF MILD, SEVERE, AND TOTAL HAYFEVER SYMPTOMS FOR THREE TREATMENT GROUPS

Group 1 = TP5 - Subcutaneous
Group 2 = TP5 - Intravenous
Group 3 = Placebo

| Average # Weekly Symptoms | Mild | Severe | Total |
|---|---|---|---|
| Group 1 to 3: | | | |
| Group 1 | 10.20 | 2.64 | 12.84 |
| Group 3 | 13.90 | 5.32 | 19.22 |
| Value of t | −1.05 | −1.55 | −1.55 |
| p-Value | .3059 | .1382 | .1394 |
| Group 2 to 3: | | | |
| Group 2 | 7.43 | 1.77 | 9.20 |
| Group 3 | 13.90 | 5.32 | 19.22 |
| Value of t | −2.43 | −2.48 | −2.70 |
| p-Value | .0257 | .0232 | .0145 |
| Group 1 to 2: | | | |
| Group 1 | 10.20 | 2.64 | 12.84 |
| Group 2 | 7.43 | 1.77 | 9.20 |
| Value of t | .79 | .60 | .92 |
| p-Value | .4377 | .5551 | .3681 |

TABLE II

AVERAGE WEEKLY NUMBER OF MILD, SEVERE, AND TOTAL SYMPTOMS BY GROUP AND WEEK

| Week: | Group 2 TP5 i.v. | Group 1 TP5 s.c. | Group 3 placebo |
|---|---|---|---|
| Total Mild Symptoms | | | |
| 3 | 4.43 | 5.22 | 12.20 |
| 4 | 8.43 | 8.11 | 10.40 |
| 5 | 6.71 | 9.00 | 12.50 |
| 6 | 9.29 | 10.11 | 15.10 |
| 7 | 8.00 | 13.11 | 21.10 |
| 8 | 8.57 | 14.44 | 18.80 |
| 9 | 7.71 | 18.56 | 20.20 |
| 10 | 4.71 | 15.22 | 14.10 |
| 11 | 5.14 | 13.11 | 9.50 |
| 12 | 1.57 | 5.67 | 5.10 |
| Total Severe Symptoms | | | |
| 3 | 1.0 | 0.56 | 5.90 |
| 4 | 0.43 | 1.11 | 4.20 |
| 5 | 0.29 | 0.78 | 4.10 |
| 6 | 1.57 | 1.44 | 6.80 |
| 7 | 1.00 | 1.33 | 6.90 |
| 8 | 2.43 | 1.89 | 9.60 |
| 9 | 0.43 | 1.11 | 8.90 |
| 10 | 0.43 | 2.56 | 2.70 |
| 11 | 0.29 | 3.78 | 2.60 |
| 12 | 0.14 | 0.22 | 1.50 |
| Total Mild & Severe Symptoms Combined | | | |
| 3 | 5.43 | 5.78 | 18.10 |
| 4 | 8.86 | 9.22 | 14.60 |
| 5 | 7.00 | 9.78 | 16.60 |
| 6 | 10.86 | 11.56 | 21.90 |
| 7 | 9.00 | 14.44 | 28.00 |
| 8 | 11.00 | 16.33 | 28.40 |
| 9 | 8.14 | 19.67 | 29.10 |
| 10 | 5.14 | 17.78 | 16.80 |
| 11 | 5.43 | 16.89 | 12.10 |
| 12 | 1.71 | 5.89 | 6.60 |

TABLE III

AVERAGE NUMBER OF SYMPTOMS PER WEEK PER SUBJECT BY TYPE OF SYMPTOM AND GROUP

| | Sneezing | | Runny Nose | | Red Eyes | |
|---|---|---|---|---|---|---|
| | Mild | Sev. | Mild | Sev. | Mild | Sev. |
| Group 2 (TP5 iv) | 2.33 | 0.61 | 3.03 | 0.80 | 0.75 | 0.08 |
| Group 1 (TP5 sc) | 2.97 | 0.46 | 3.51 | 1.86 | 1.12 | 0.12 |
| Group 3 (placebo) | 3.89 | 1.45 | 5.13 | 2.68 | 1.36 | 0.05 |

| | Itchy Eyes | | Cough | | All Symptoms | |
|---|---|---|---|---|---|---|
| | Mild | Sev. | Mild | Sev. | Mild | Sev. |
| Group 2 (TP5 iv) | 0.84 | 0.25 | 0.48 | 0.03 | 7.43 | 1.77 |
| Group 1 (Tp5 sc) | 2.45 | 0.18 | 0.14 | 0.02 | 10.20 | 2.64 |
| Group 3 (Placebo) | 2.19 | 0.98 | 1.33 | 0.16 | 13.90 | 5.32 |

What is claimed is:

1. A method of palliating, in a human, the sneezing, runny nose, red eyes, itchy eyes or cough symptoms of type I hypersensitivity to environmental antigens resulting from the action of mediators released when IgE antibodies react with said antigens comprising administering to said human an effective symptom palliating amount of thymopentin or a pharmaceutically-acceptable salt thereof.

2. The method of claim 1 wherein the symptoms are the symptoms of allergic rhinitis.

3. The method of claim 1 wherein the symptoms are the symptoms of hay fever.

4. The method of claim 1 wherein the method of administration is parenteral.

5. The method of claim 4 wherein the method of administration is intravenous or subcutaneous.

6. A method of palliating the symptoms of allergic rhinitis in a human having said symptoms which comprises administering to said human by intravenous injection an effective allergy palliating amount of thymopentin or a pharmaceutically-acceptable salt thereof.

7. The method of claim 6 wherein the effective amount is from about 50 mg to about 700 mg.

8. The method of claim 6 wherein the effective amount is about 100 mg administered once per week.

9. A method for palliating the symptoms of allergic rhinitis in a human having said symptoms which comprises administering to said human by subcutaneous injection an effective allergy palliating amount of thymopentin or a pharmaceutically-acceptable salt thereof.

10. The method of claim 9 wherein the effective amount is about 50 mg administered three times per week.

* * * * *